United States Patent [19]
Kim

[11] Patent Number: 5,549,543
[45] Date of Patent: Aug. 27, 1996

[54] LAPAROSCOPIC DEFOGGING APPARATUS

[76] Inventor: Il G. Kim, Box 15A, R.R. #1, Hughesville, Pa. 17737

[21] Appl. No.: 457,012

[22] Filed: Jun. 1, 1995

[51] Int. Cl.$^6$ .................................................... A61B 1/06
[52] U.S. Cl. ......................... 600/169; 600/102; 392/433
[58] Field of Search .................................. 600/133, 169, 600/102, 220, 198; 604/113, 291; 206/438; 219/209, 210, 220, 385, 386, 429, 433; 392/341, 443, 445, 418

[56] References Cited

U.S. PATENT DOCUMENTS

| | | |
|---|---|---|
| 3,980,078 | 9/1976 | Tominaga . |
| 4,132,227 | 1/1979 | Ibe . |
| 4,256,697 | 3/1981 | Baldwin .............................. 219/433 X |
| 5,167,220 | 12/1992 | Brown . |
| 5,225,001 | 7/1993 | Manni et al. . |
| 5,237,984 | 8/1993 | Williams, III et al. . |
| 5,290,168 | 3/1994 | Cooper et al. . |
| 5,351,675 | 10/1994 | Brodsky ...................................... 128/4 |
| 5,392,766 | 2/1995 | Masteson et al. . |

FOREIGN PATENT DOCUMENTS 1618399  1/1991  U.S.S.R. .

*Primary Examiner*—Linda C. Dvorak
*Assistant Examiner*—Beverly M. Flanagan
*Attorney, Agent, or Firm*—Thomas R. Shaffer, Esq.

[57] ABSTRACT

A laparoscopic defogging apparatus for regulating and maintaining the temperature of a lens and end portion of the laparoscope is disclosed. A receptacle is provided which contains a first sterile fluid at a sufficient depth to allow the lens and end portion of the laparoscope to be placed in thermal contact with the first sterile fluid. A container is provided into which the receptacle is placed, which container is adapted to receive and contain a second sterile fluid at a sufficient depth to provide thermal contact with at least a part of the receptacle side wall portion. A heating device is provided to heat the sterile fluids whereby the laparoscope is maintained at a constant desired temperature, thereby preventing lens fogging.

16 Claims, 3 Drawing Sheets

LAPAROSCOPIC DEFOGGING APPARATUS

BACKGROUND OF THE INVENTION

1. Field the Invention

This invention relates to a laparoscopic defogging apparatus. More specifically, it relates to a defogging apparatus wherein the lens and end portion of a laparoscope are immersed prior to use in a heated sterile fluid contained in a hand held receptacle.

2. Description of the Prior Art

It is well known to surgeons who routinely use endoscopes or laparoscopes that fogging of the lens occurs during a medical examination due to the differences in temperature between the scope and the living body in which the laparoscope is inserted. Fogging typically occurs when the lens of the end portion of the laparoscope is cold enough to condense moisture in the immediate vicinity of view such as when a laparoscope at room temperature (i.e., 68° F.) is placed in the vicinity of warm moist tissue. The relatively large metallic mass of the barrel of the laparoscope keeps the laparoscope lens at a cool temperature for an extended period of time even though the laparoscope is in contact with the warm surrounding tissue during examination.

A variety of solutions have been proposed for the above problem. One solution, as set forth in Williams, III et al., U.S. Pat. No. 5,237,984, is to provide a separate sheath member 10 which provides thermal insulation that creates a desirable thermal gradient between the endoscope lens 38 and the endoscope lens cover 14. The endoscope lens cover portion 14 can thus be warmed by the body relatively quickly to the temperature of the viewing surroundings. Williams also suggests the application of a known anti-fog component in the resin used to form the lens cover 14, or on to the cap section 16 during manufacture. While such a method may provide some thermal insulation, the proposed solution does not address the cause of the problem.

Masterson et al., U.S. Pat. No. 5,392,766, discloses the provision of a separate cleaning element which allows for in situ cleaning during a surgical procedure. Such a solution, while effective, requires replacement of existing laparoscopes and endoscopes which are extremely costly.

Others have suggested cleaning the lens by flushing with various cleansing solutions (see U.S. Pat. Nos. 5,225,001; 4,132,227; 5,167,220; 3,980,078; and 5,290,168) or by flushing with a gaseous flow (see U.S. Pat. Nos. 4,760,840 and 3,941,120). Finally, Soviet Union reference 1618-399A1 discloses a laser catheter which includes a complex cooling system.

None of the above described patents provide a solution to the problem but rather, by complex and expensive methods, merely attempt to minimize the effects of the problem.

SUMMARY OF THE INVENTION

The present invention provides a unique solution to the previously identified problem by regulating and maintaining the temperature of the lens and end portion of a laparoscope at a desired temperature prior to use during surgery. By heating the lens and end portion of the laparoscope to a desired temperature, preferably 102° F., the temperature gradation which causes the fogging is substantially eliminated.

Applicant provides a laparoscopic defogging apparatus which includes a receptacle having a receptacle base, a receptacle side wall portion and a receptacle cover. The receptacle cover has an opening therein sized to receive the lens and end portion of the laparoscope. The receptacle is adapted to receive and contain a first sterile fluid at a sufficient depth to allow the lens and end portion of a laparoscope to be placed into thermal contact with the first sterile fluid.

A container is also provided which has a container base, a container side wall portion and a container cover. The container cover is provided with an opening therein sized to receive the receptacle. The container is adapted to receive and contain a second sterile fluid at a sufficient depth to provide thermal contact with at least a part of the receptacle side wall portion. Preferably, both the first and second sterile fluids consist of water although any other sterile fluid which would not adversely affect a patient may be used, such as a saline solution.

A heating means which is connected to an energy source is placed into thermal contact with the container whereby the heating means provides sufficient heat to the container such that the first sterile fluid is maintained at a desired temperature, preferably in the range of approximately 100° F. to 104° F. with a preferred temperature of 102°. The heating means can consist of a device commonly known as a "hot plate" or "warming plate" of the type utilized to keep beverages, such as coffee, at a desired temperature. Preferably, such a device has a temperature control to provide and regulate a sufficient amount of heat to the container which will be thermally conducted to the first sterile fluid in the receptacle to heat and maintain such fluid at the desired temperature.

The receptacle is preferably sized and shaped so as to be conveniently hand held by a surgeon during the procedure. The receptacle is hand carried to the operating room table. The laparoscope is then inserted into the receptacle. The temperature of the water in the receptacle is then automatically transmitted to the metal laparoscope. The receptacle cover preferably has a cap attached to the receptacle cover so that when the laparoscope is removed from the receptacle, the cap can be placed over the receptacle cover opening to prevent contamination and evaporation of the first sterile fluid therein contained.

In a preferred form of the present invention, the receptacle cover is removably attached to the receptacle side wall portion in the form of a push-on cap or similar means. However, the receptacle cover may be integrally formed as a single component with the receptacle side wall portion.

The receptacle is preferably formed from a sterile plastic material and preferably has a cylindrical shape.

The container is likewise preferably formed of a sterile plastic material and may have a cylindrical shape. In one embodiment of the invention, the container is provided with a side wall portion which has a frusto-conical shape which provides added stability when the container is placed upon the heating means making it less likely that the container would tip over.

It will be obvious to those skilled in the art that the receptacle and the container as well as the first and second sterile fluids contained therein must be sterile such that both the interior and exterior of the receptacle will be sterile and will not contaminate either the laparoscope or the surgeon's sterile gloves. Because of the need to create and maintain a sterile field during any surgical or medical examination procedure utilizing the laparoscope, preferably the receptacle and container are designed to be completely disposable and are discarded after each surgical procedure and replaced with a new receptacle and container. It is preferable that both the receptacle and container be formed of a transparent or translucent sterile plastic material so that the fluid level in each such container can be observed. Although a plastic material is desired, the invention will still provide an effective result if a glass or other non-porous material is utilized instead of plastic.

The heating means specifically includes a heating surface which, in one embodiment of the invention, is placed into direct physical contact with the container base. Thus, the plastic material selected must be resistant to melting at a temperature at which the heating surface is heated.

In the embodiment of the present invention as thus far described, the container and the receptacle are preferably initially filled from a sterile source of water which is typically available in most operating rooms at a temperature of approximately 104°. The heating means provides sufficient heat to maintain the temperature of the fluid in the receptacle at a constant temperature of approximately 102° to 104° F. It will be obvious to those skilled in the art that the control of the temperature at the desired level can be accomplished in a number of ways. First, the heating means itself may and preferably does have a temperature and control adjusting means. Other factors which will affect the temperature of the first sterile fluid in the receptacle include the diameter, height and depth to which the receptacle and container are filled with a sterile fluid. For example, a tall receptacle which protrudes far above the liquid in the container would cool more quickly than a shorter receptacle which is completely immersed in the container liquid.

A second embodiment of the invention, adapted for use where a readily available source of preheated sterile water is not available, further con, rises a vessel, a cold water heating device and a heating surface. In this embodiment, the vessel includes a vessel base, a vessel side wall portion and a vessel cover. The vessel cover has an opening therein sized to receive the container. The vessel is adapted to receive heated water from the cold water heating device to a sufficient depth to provide thermal contact with at least a part of the container side wall portion. In this embodiment, the vessel base is placed into direct contact with the heating surface. In concept, the heating means in this embodiment of the invention would have a form similar to a standard drip coffee machine which includes a cold water storage tank, a heating element and a pump. Such a cold water heating device would be regulated to provide a source of a means to heat cold water to be placed into the vessel at a temperature of approximately 110°.

BRIEF DESCRIPTION OF THE DRAWINGS

The invention will now be explained in detail with reference to the accompanying drawings in which.

DETAILED DESCRIPTION OF THE PREFERRED EMBODIMENTS

Figure 1:
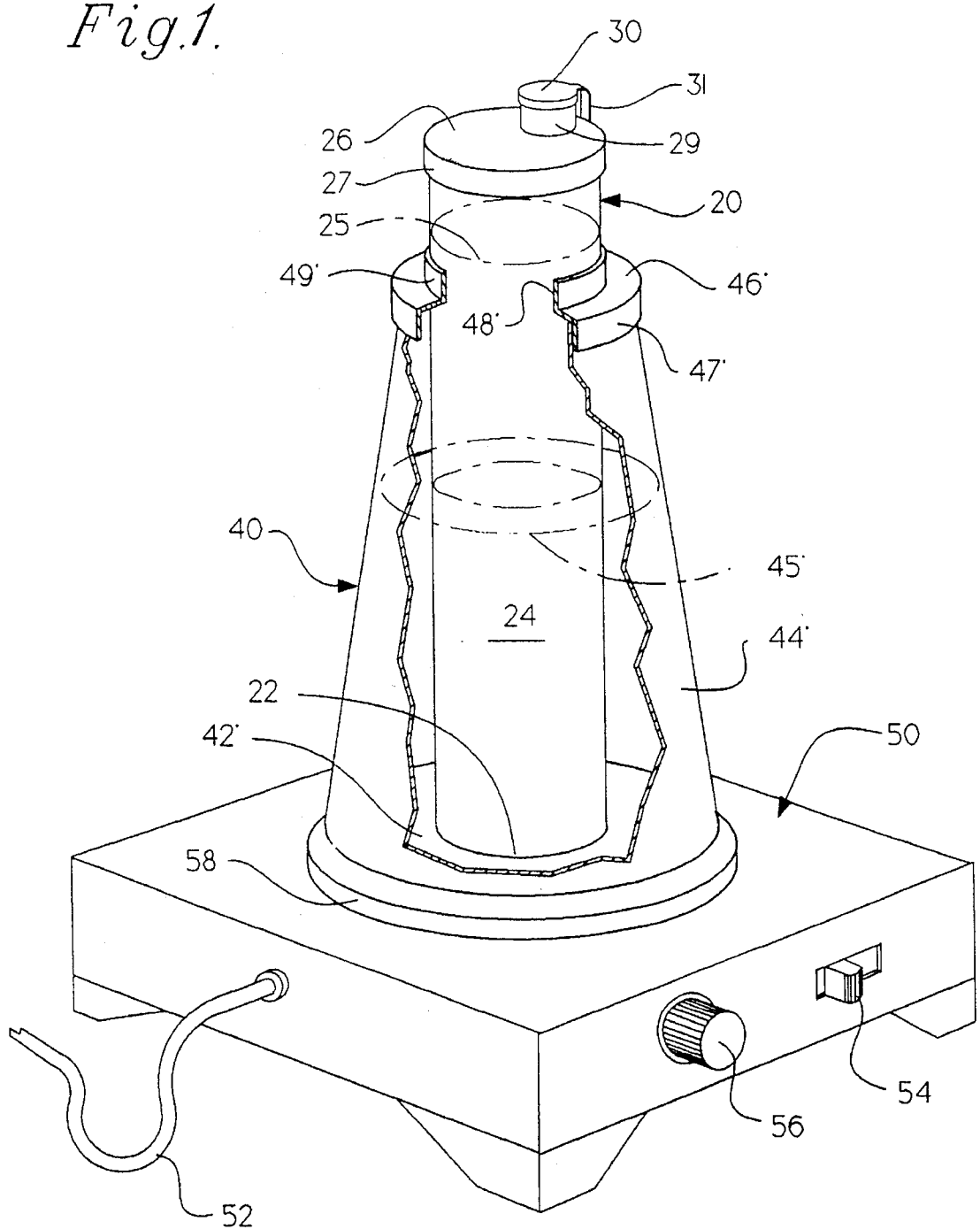
FIG. 1 is an isometric view of a first embodiment of the present invention showing the receptacle, container and heating means.
Figure 3:
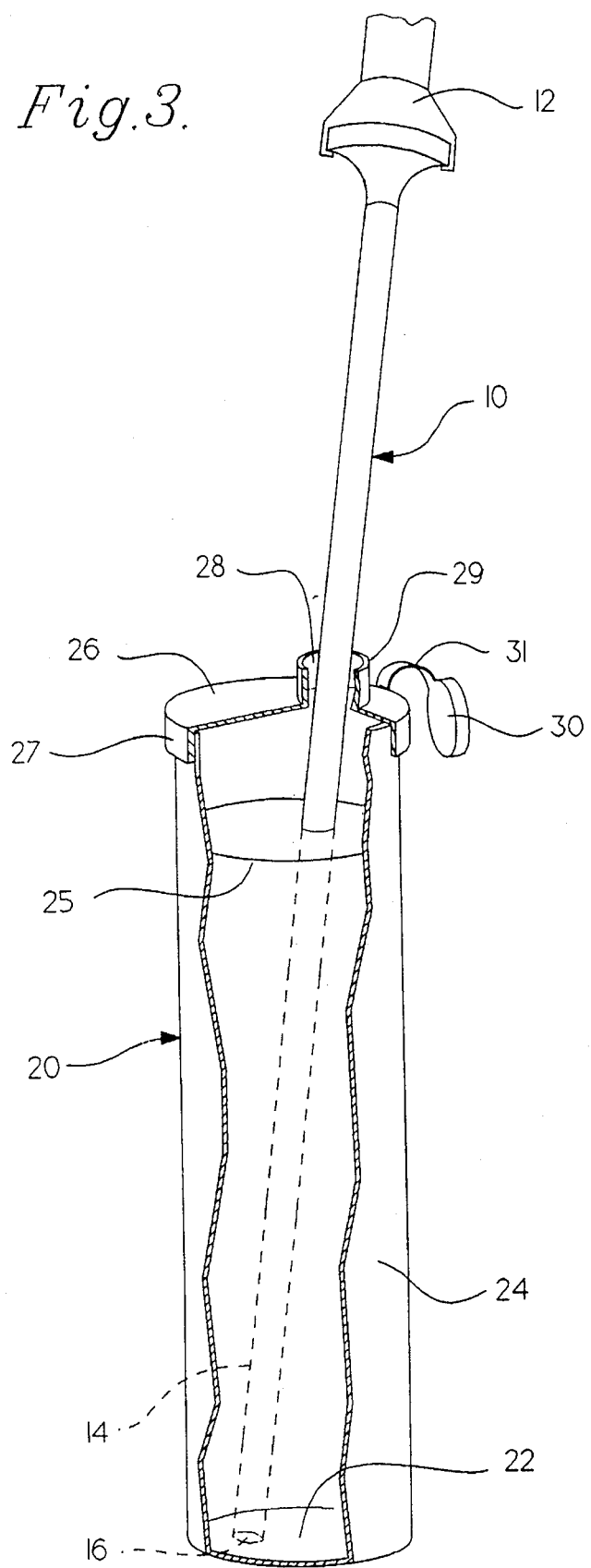
FIG. 3 shows the receptacle of FIGS. 1 and 2 as removed from the respective containers and into which a laparoscope is positioned.

Referring to FIG. 1, a laparoscope defogging apparatus for regulating and maintaining the temperature of a lens and end portion of a laparoscope is shown. A receptacle 20 having a receptacle base portion 22, a cylindrical receptacle side wall portion 24 and receptacle cover portion 26 is disclosed. The receptacle cover includes a downwardly extending annular flange 27 utilized to attach by threading or other means the cover 26 to the cylindrical receptacle side wall portion 24. As shown in FIG. 3 the receptacle cover 26 is also provided with an opening 28 therein sized to receive the lens and end portion of a laparoscope. A cap 30 which is attached by arm 31 is provided to cover opening 28 when the laparoscope is not inserted in said receptacle 20. Receptacle 20 is adapted to receive a first sterile fluid to a depth 25 as shown.

A container 40 is provided which has a container base portion 42', a frusto-conical side wall portion 44' and a container cover 46' which is attached to the container side wall portion 44' by means of a downwardly extending annular flange 47' provided on said container cover 46'. The container cover 46' has an opening 48' therein sized to receive and contain the receptacle 20. An upwardly extending annular flange 49' is provided surrounding said opening 48' to provide additional support for the receptacle 20 which is sized to removably slide in and out of opening 48' into container 40.

In this embodiment of the invention, the container base portion 42' is adapted to be placed in direct physical contact with a heating surface 58 of heating means 50. Heating means 50 includes an electrical cord 52 utilized to connect the heating means to a source of electrical power, an on/off switch 54 and a temperature control adjusting means 56.

The receptacle base portion 22 may be adapted to rest in direct contact with the container base portion 42' as shown or, the receptacle base portion 22 may be provided with short legs (not shown) to provide a slight spacing of the receptacle base portion 22 from the container base portion 42'.

The container is provided with a second sterile fluid to a level 45' as shown in the figure.

In use, preheated sterile water or other sterile fluid from a readily available source in the operating room is provided into receptacle 20 and container 40 to the levels as previously described. Preferably, as initially placed therein, the temperature of the sterile fluids is approximately 104° each. After the temperature stabilizes, the temperature of the second sterile fluid 45' will stabilize at approximately 104° F. with the temperature of the first sterile fluid 25 stabilizing at a temperature of approximately 102° F.

Preferably, the receptacle base portion 22 has a diameter of approximately 5 centimeters and the receptacle 20 has an overall height of 17 centimeters. Preferably, the container base portion 42 has a diameter of approximately 11 centimeters so that it will accurately rest upon the heating surface 58 of the heating means 50, which heating surface 58 preferably has a diameter of approximately 12.5 centimeters. The container preferably has an overall height of 14 centimeters. The upper part of the container is 7 centimeters in diameter. The opening 28 in the receptacle cover preferably is approximately 1.5 centimeters sized to receive the lens and end barrel portion of the laparoscope.

Figure 2:
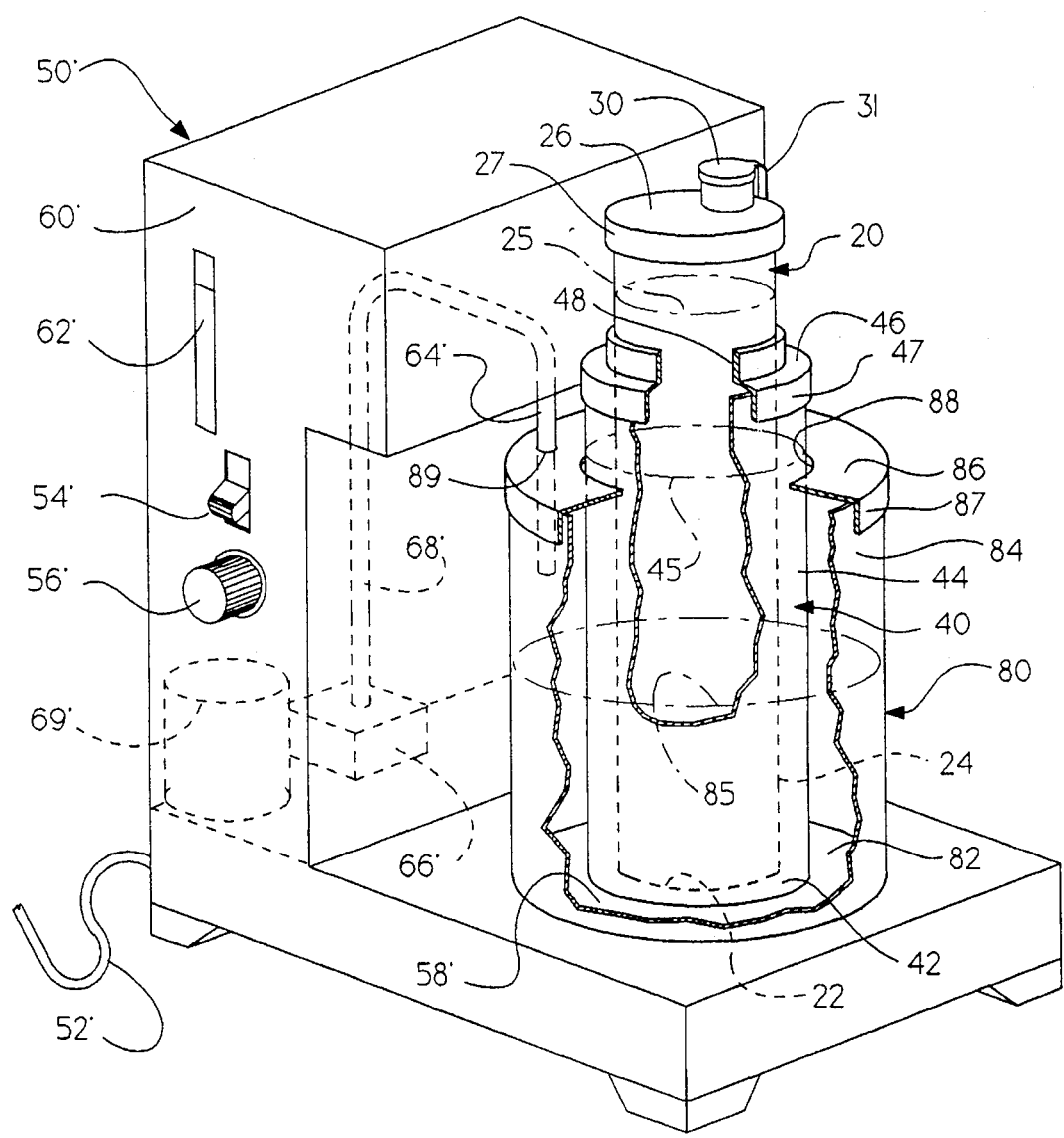
FIG. 2 is an isometric view of a second embodiment of the present invention showing the receptacle, container, vessel and modified heating means which includes a cold water heating device.

Referring to FIG. 2, a second embodiment of the present invention is shown. In this embodiment, like components bear the same reference numerals or if like components are not identical, will bear the same numerals indicated as prime numbers. The receptacle 20 is identical to that previously described. In this embodiment, however, the container 40 has a base portion 42, cylindrical side wall portion 44 and a cover portion 46. The receptacle is filled with a sterile fluid to level 25 and the container is filled with a second sterile fluid to a level 45. This embodiment of the invention further comprises a vessel 80 which includes a vessel base portion 82, cylindrical vessel side wall 84 and a vessel cover 86 which is attached by means of a downwardly extending annular flange 87. The vessel cover 86 has an opening 88 therein sized to receive the container 40. The vessel cover 86 also has a small opening 89 therein sized to receive heated water through an outlet 64' of a modified heating means 50. In this embodiment, the vessel has a height dimension of 14 centimeters and a vessel diameter of 11 centimeters. Further, the container in this embodiment which is cylindrical in shape has a diameter of approximately 7 centimeters.

In this embodiment, a modified heating means 50 is provided which includes an electrical cord 52' adapted to connect the heating means to a source of electrical power, an on/off switch 54' and a temperature adjusting means 56'. The modified heating means 50 includes a cold water storage tank 60', including a visual fluid level window 62'. Cold water is placed into the cold water storage tank 60 and is heated by heating element 69' and pumped by pump 66' through conduit 68' to outlet 64'. The outlet 64' provides water preferably heated to a temperature of approximately 110° into the vessel 80 to a level 85. The heating means 50 also includes a heating surface 58 which is designed to provide sufficient heat to maintain the temperature of the first sterile fluid 25 at a desired temperature of approximately 102° F. In this embodiment, of the invention, because of the diameters, height and cooling capacities, it is envisioned that the temperature of the water placed into the vessel may stabilize at approximately 110° F., the second sterile fluid within the container may stabilize at approximately 104° F. and that the first sterile fluid within the receptacle will stabilize at approximately 102° F.

Referring to FIG. 3, the removable receptacle 20 is shown separate and apart from the other elements of the invention. In FIG. 3, a laparoscope 10 having a handle portion 12, end portion 14 and lens 16 is shown as inserted through opening 28 of receptacle cover 26 and supported by upwardly extending annular flange 29 of receptacle cover 26. In use, the operating room nurse would carry the receptacle as shown in FIG. 3 directly to the operating table. The laparoscope is then inserted into the receptacle opening. The temperature of the water is then automatically transmitted to the metal laparoscope prior to inserting it into the living body.

It will be obvious to those skilled in the art that the present invention eliminates the problems associated with fogging by actually warming the temperature of the end portion 14 and lens 16 of the laparoscope prior to insertion into the living body. Therefore, there will be little or no temperature differential between the laparoscope and the warm, moist tissue and thus, little or no likelihood of fogging.

While certain presently preferred embodiments of the present invention have been described and illustrated, it is to be distinctly understood that the invention is not limited thereto and may be otherwise embodied and practiced within the scope of the following claims:

I claim:

1. A laparoscopic defogging apparatus for regulating and maintaining the temperature of a lens and end portion of a laparoscope comprising:

(a) a receptacle having a receptacle base, a receptacle side wall portion and a receptacle cover, said receptacle cover having an opening therein sized to receive the lens and end portion of a laparoscope, said receptacle adapted to receive and contain a first sterile fluid at a sufficient depth to allow the lens and end portion of a laparoscope to be placed into thermal contact with said first sterile fluid;

(b) a container having a container base, a container side wall portion and a container cover, said container cover having an opening therein sized to receive said receptacle, said container adapted to receive and contain a second sterile fluid at a sufficient depth to provide thermal contact with at least a part of said receptacle side wall portion; and (c) a heating means connected to an energy source and in thermal contact with said container whereby said heating means provides sufficient heat to maintain said first sterile fluid at a desired temperature.

2. A laparoscopic defogging apparatus according to claim 1 wherein said receptacle is removable from said container and is sized to be hand-held.

3. A laparoscopic defogging apparatus according to claim 1 further comprising a cap for covering said receptacle cover opening.

4. A laparoscopic defogging apparatus according to claim 3 wherein said cap is attached to said receptacle cover.

5. A laparoscopic defogging apparatus according to claim 1 wherein said receptacle cover is removably attached to said receptacle side wall portion.

6. A laparoscopic defogging apparatus according to claim 1 wherein said receptacle cover opening supports said laparoscope in an upright position within said receptacle.

7. A laparoscopic defogging apparatus according to claim 6 wherein said receptacle cover has a flange surrounding said receptacle cover opening whereby said flange aids in supporting said laparoscope.

8. A laparoscopic defogging apparatus according to claim 1 wherein said receptacle is formed of a sterile plastic material.

9. A laparoscopic defogging apparatus according to claim 1 wherein said receptacle has a cylindrical shape.

10. A laparoscopic defogging apparatus according to claim 1 wherein said container is formed of a sterile plastic material.

11. A laparoscopic defogging apparatus according to claim 1 wherein said container has a cylindrical shape.

12. A laparoscopic defogging apparatus according to claim 1 wherein said container has a frusto-conical shape.

13. A laparoscopic defogging apparatus according to claim 1 wherein said heating means further comprises a heating surface in direct physical contact with said container base.

14. A laparoscopic defogging apparatus according to claim 1 wherein said heating means further comprises a vessel, a cold water heating device and a heating surface, said vessel having a vessel base, a vessel side wall portion and a vessel cover, said vessel cover having an opening therein sized to receive said container, said vessel adapted to receive heated water from said cold water heating device to sufficient depth to provide thermal contact with at least a part of said container side wall portion.

15. A laparoscopic defogging apparatus according to claim 1 wherein said vessel base is in direct physical contact with said heating surface.

16. A laparoscopic defogging apparatus according to claim 1 wherein said cold water heating device further comprises a cold water storage tank, a heating element and a pump.

* * * * *

UNITED STATES PATENT AND TRADEMARK OFFICE
CERTIFICATE OF CORRECTION

PATENT NO.   :   5,549,543
DATED        :   August 27, 1996
INVENTOR(S) :    Il G. Kim It is certified that error appears in the above-identified patent and that said Letters Patent is hereby corrected as shown below:

Column 3, line 32, change "con,rises" to --comprises--.

Signed and Sealed this

Fourth Day of November, 1997

Attest:

BRUCE LEHMAN

*Attesting Officer*     *Commissioner of Patents and Trademarks*